United States Patent [19]

Lavender et al.

[11] Patent Number: 4,592,582
[45] Date of Patent: Jun. 3, 1986

[54] BAG CLAMPING ARRANGEMENT

[75] Inventors: Ardis R. Lavender, Chappaqua; George Vrany, Bedford Hills, both of N.Y.

[73] Assignee: USV Pharmaceutical Corporation, Tuckahoe, N.Y.

[21] Appl. No.: 684,020

[22] Filed: Dec. 20, 1984

[51] Int. Cl.$^4$ .......................... A61M 1/00; B04B 5/00; B65D 31/12

[52] U.S. Cl. .................................. 294/137; 294/159; 604/322; 604/410; 383/38

[58] Field of Search ............... 294/137, 159, 160, 162, 294/163, 103.1; 383/35, 38, 39, 40; 604/322, 410; 248/101; 232/43.2; 220/404

[56] References Cited

U.S. PATENT DOCUMENTS 3,149,943 9/1964 Amador ................................. 383/38
3,809,224 5/1974 Greenwood ......................... 383/38

Primary Examiner—James B. Marbert
Attorney, Agent, or Firm—Scully, Scott, Murphy & Presser

[57] ABSTRACT

A bag clamping arrangement, such as an arrangement for automatically controlling the filling volume and overflow of a liquid conducted into a flexible bag which is clamped in the arrangement. The bag clamping arrangement is essentially constituted of a rigid upwardly open receptacle of substantially rectangular or a relatively large upper compartment, and wherein a narrow compartment which in open communication with the upper compartment depends downwardly from the bottom of the upper compartment so as to extend longitudinally and generally centrally across the full width of the receptacle. The lower compartment includes opposite parallel sidewalls which are down so as to form a reducing compartment width therebetween. Towards the lower end of the compartment is a plate-like clamping arrangement essentially constituted of a flat plate member which may be manually engaged through an elongate slot and gripping portion proximate its upper horizontal edge. The plate member is provided along its lower edge on both sides thereof with sideways projecting resilient clamping components which, upon being inserted into the lower compartment of the receptacle, are biased towards the plate member and are dimensioned to clampingly engage between the sides of the clamping plate and the contiguous sidewalls of the lower compartment. A flexible bag is positioned on either one side, or two bags each respectively on the opposite sides of the clamping plate member prior to insertion of the latter into the receptacle, with the lower end portion of the bag or bags extending between the respective resilient clamping component and the facing surface of the clamping plate member such that, upon introduction of the clamping plate member downwardly into the lower compartment, the applicable resilient clamping component upon being biased towards the plate member, will clamp the lower bag portion against the facing surface of the clamping plate member, thereby ensuring the secure clamping of the bag.

17 Claims, 6 Drawing Figures

BAG CLAMPING ARRANGEMENT

BACKGROUND OF THE INVENTION

1. Field of the Invention

The present invention relates to a bag clamping arrangement and, more particularly, an arrangement for automatically controlling the filling volume and overflow of a liquid conducted into a flexible bag which is clamped in the arrangement.

The conveyance into and collection of fluids or liquids in sealed flexible bags constituted of a liquid-impervious material at times necessitates the application of controls for handling any encountered overflow of such fluids. For instance, in certain applications, such as when directing urine from an indwelling catheter towards a plastic bag, the flow of the urine into the bag will generally cease upon the bag having been filled, thereby producing an adverse effect on the urinary functions. Current bag replacing practice necessitates the operative steps of either the disconnection of the filled bag and consequently replacement with a second empty bag, or the employment of an automatic or semi-automatic mechanical device for diverting the flow of urine or fluid from the filled bag which emanates from the catheter to a second empty bag. Thus, the replacement of a filled bag by manually disconnecting it from a catheter is encumbered with the risk of contamination by the fluid in the flow system; thereby requiring frequent inspection by operating personnel for the presence of any possible overflow and is, moreover, difficult and cumbersome to implement in actual practice. Additionally, mechanical overflow diversion devices or systems are generally complicated in structure and function, uneconomically expensive, and at times tend to fail during operation so as not to afford a sufficient degree of reliability.

Similarly, a bag clamping arrangement of the type described hereinabove may be required, upon occasion, for automatically diverting plasma from one flexible bag to another bag during the collection of plasma from a plasmapheresis device. In that instance, important requirements are the maintenance of a closed flow system for the plasma collection during its operation, a high degree of simplicity in operation, and ease of manufacture so as to render it economical. Frequently, any plasma which is collected in the flexible bag is subsequently rapidly processed through the quick freezing of the contents, in effect, the plasma, which necessitates that the liquid contents be present in a thin layer within the bag. Consequently, any flexible bag employed in such a plasma collecting system should be only filled to a proportion or certain percentage of its available fill volume, in contrast as would be the case for simple fluid containment, such as urine collection. In view of the foregoing, the inventive clamping arrangement also incorporates structural and functional features which will facilitate that the bag be filled with fluid or liquid up to only a predetermined part of its volume and in which any overflow may be diverted to a second bag which is similarly clamped in the bag clamping arrangement and connected to the first bag.

2. Discussion of the Prior Art

Although various types of bag clamping devices and arrangements are known in the art, none of these are adapted in any manner for the automatic control over the filling volume of flexible or plastic bags and the overflow of a fluid or liquid from such bags.

Schweizer U.S. Pat. No. 4,449,969 discloses a drainage receptacle construction for collecting body fluids having a support frame, wherein a flexible collecting bag is suspended from upright posts through eyelets which are formed in the bag for maintaining the vertical position of the bag, and which includes a clamping device engaging the lower end of the bag. Although this structure is utilized in connection with a drainage device for collecting urine from a patient, it fails to provide for the necessary control of the overflow of fluid from the filled bag and, in effect, necessitates that the filled bag be manually disconnected from a catheter communicating therewith, and thereafter be replaced by an empty bag which is then connected to the catheter.

Other bag holders and various types of bag clamping devices are disclosed in Benoit U.S. Pat. No. 3,653,620; Heitz U.S. Pat. No. 3,779,419; Larson U.S. Pat. No. 3,297,287; and Kleeberg U.S. Pat. No. 3,443,745. Although all of these U.S. patents disclose bag holding and clamping devices, none of these fulfill functions analogous to the inventive bag clamping arrangement which provides for the automatic control of the filling volume and/or overflow of fluids or liquids from a partly filled bag into a second empty bag retained in the clamping arrangement.

SUMMARY OF THE INVENTION

In order to fulfill the desired functions of automatically controlling the filling volume of flexible bags and overflow of fluids or liquids from the flexible bags when employed as discussed hereinabove, the present invention contemplates the provision of a bag clamping arrangement which is essentially constituted of a rigid upwardly open receptacle of substantially rectangular or a relatively large upper compartment, and wherein a narrow compartment which is in open communication with the upper compartment depends downwardly from the bottom of the upper compartment so as to extend longitudinally and generally centrally across the full width of the receptacle. The lower compartment includes opposite parallel sidewalls which are stepped down so as to form a reducing compartment width therebetween towards the lower end of the lower compartment. Insertable into the lower compartment by being moved vertically downwardly through the upper compartment of the receptacle, is a plate-like clamping unit essentially constituted of a flat plate member which may be manually engaged through an elongate slot and gripping portion formed proximate its upper horizontal edge. The plate member is provided along its lower edge on both sides thereof with sideways projecting resilient clamping components which, upon being inserted into the lower compartment of the receptacle, are biased towards the plate member and are dimensioned to clampingly engage between the sides of the clamping plate and the contiguous sidewalls of the lower compartment. A flexible bag is positioned on either one side, or two bags each respectively on the opposite sides of the clamping plate member prior to insertion of the latter into the receptacle, with the lower end portion of the bag or bags extending between the respective resilient clamping component and the facing surface of the clamping plate member such that, upon introduction of the clamping plate member downwardly into the lower compartment, the applicable resilient clamping component upon being biased towards the plate member, will clamp the lower bag portion against the facing surface of the clamping plate member, thereby ensuring the secure clamping of the bag, while concurrently forming a seal at the clamping location inhibiting any liquid being filled into the upper portion of the flexible bag from flowing into the lower portion of the bag beyond the location at which the bag is clamped between the resilient clamping component and the clamping plate member. Consequently, the fill volume of the fluid or liquid conducted into the portion of the flexible bag which is located above the clamping location can be varied or adjusted in dependence upon the proportion of the bag which is clamped off by the resilient clamping component and the clamping plate member.

Furthermore, in order to obviate the necessity for having to immediately remove and replace the flexible bag when the upper portion thereof is filled with a fluid, for instance, when the bag is connected to a catheter, the bag may be connected to a second flexible bag which is arranged on the opposite side of the clamping plate member in the upper compartment of the receptacle, and wherein the second bag is clamped in a manner similar to the clamping of the first bag between a resilient clamping component on the other side of the clamping plate member and the opposing surface of the clamping plate member. This will eliminate the necessity for the immediate disconnection of the first bag upon being filled with fluid as in the prior art devices described hereinabove.

When the clamping arrangement is utilized for the collection of plasma, for instance, if only one flexible collecting bag is employed, and only a relatively small proportion of the bag is to be filled with plasma so as to enable the bag to be subsequently frozen with the contents forming a relatively thin layer, then the lower portion of the bag may be folded over along a predetermined fold line so as to provide a relatively large volume of bag space which remains unfilled because of the clamping action and resultant seal formed by the resilient clamping component and the clamping plate member in engagement with the bag walls.

Accordingly, it is a primary object of the present invention to provide a bag clamping arrangement of the type described hereinabove which will allow for the control over the filling volume and over any overflow of fluids or liquids which are filled into a closed flexible bag.

It is a more specific object of the present invention to provide a bag clamping arrangement of the type described, which is accomplished through the intermediary of a simply and inexpensively constructed receptacle which includes structure cooperative with a clamping plate unit for sealingly clamping the lower portions of one or more flexible bags which are arranged in the upper compartment of the receptacle so as to thereby control the amount or volume of a liquid being filled into the flexible bag.

Still another more specific object of the present invention is to provide a bag clamping arrangement as described which is inexpensively constructed, yet durable in construction and wherein bags may be readily clamped and removed therefrom and replaced by other bags in a simple and rapid manner without the hazard of exposing the bag contents to the environment.

BRIEF DESCRIPTION OF THE DRAWINGS

Reference may now be had to the following detailed description of an exemplary embodiment of the inventive bag clamping arrangement, taken in conjunction with the accompanying drawings; in which.

DETAILED DESCRIPTION

Figures 1, 6:
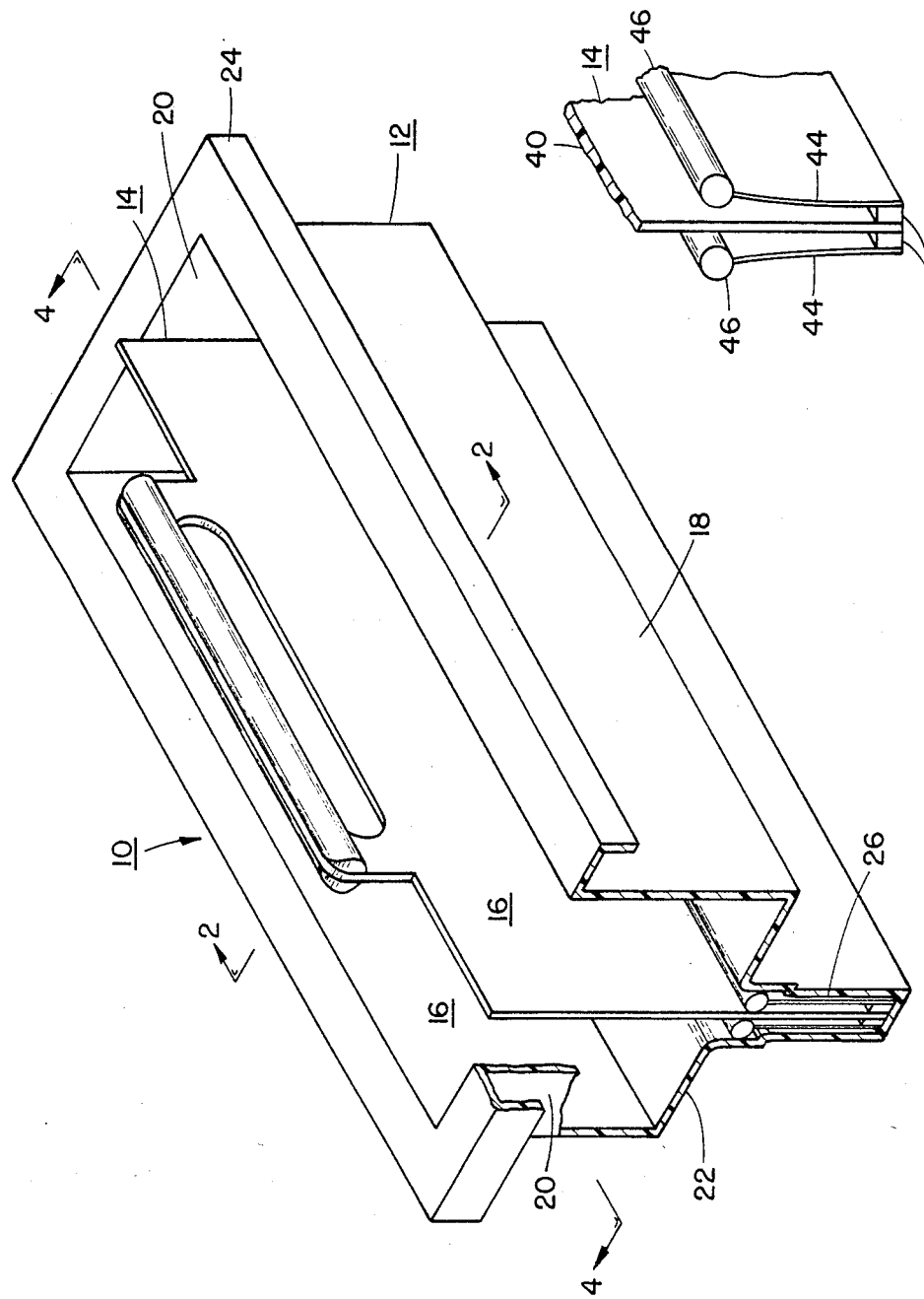
FIG. 1 illustrates a perspective view of the bag clamping arrangement, with a portion of the front wall having been omitted to illustrate the interior of the arrangement.
FIG. 6 illustrates a perspective view of the lower end portion of the clamping plate unit.

Referring now in detail to the drawings, and in particular the perspective view shown in FIG. 1, the bag clamping arrangement 10 is constituted of a receptacle 12 into which there is insertable the bag clamping plate unit 14.

The receptacle 12, as is also shown in detail in FIGS. 2 through 5 of the drawings, includes a wide upper compartment 16 which is formed by upstanding sidewalls 18 and end walls 20 and a generally flat bottom wall structure 22. Extending about the periphery of the upper edge of the side and end walls 18 and 20, is a continuous outwardly projecting flange 24 with a downturned outer lip so as to, in cross-section, assume the form of a generally inverted U-shape, for mounting on a support as described further hereinbelow. The receptacle 12, in plan view, is of an essentially parallelepiped configuration, rectangular in this instance, although other configurations also readily lend themselves to the present invention.

Figures 4, 5:
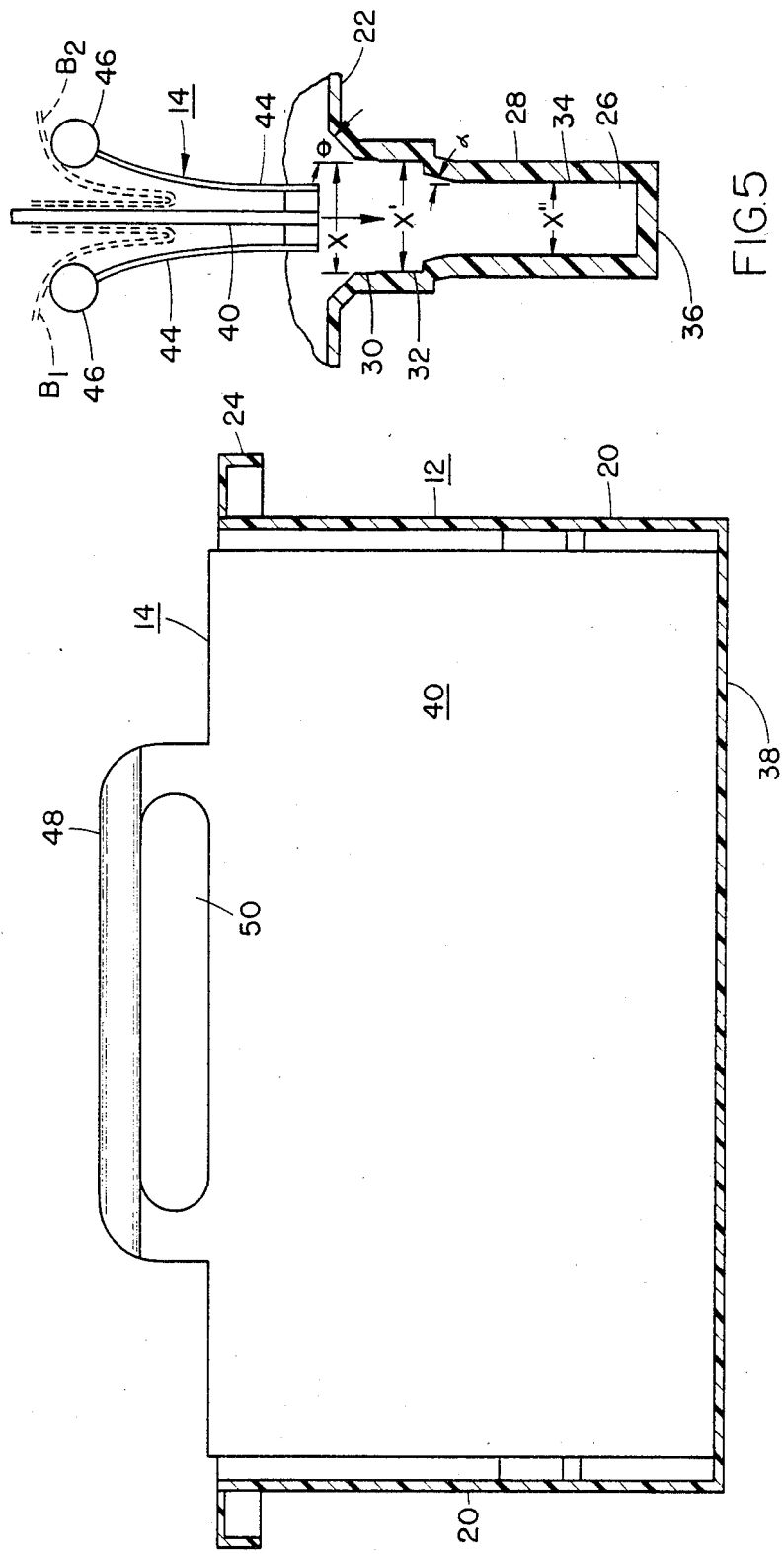
FIG. 4 illustrates a sectional view of the bag clamping arrangement taken along line 4—4 in FIG. 1.
FIG. 5 illustrates, on an enlarged scale, a sectional view through the lower compartment of the receptacle of the bag clamping arrangement, and also showing the lower end portion of the clamping plate unit prior to its insertion into the lower receptacle compartment.

Extending centrally along the bottom of the receptacle 12, across either the full length or width of the receptacle, is a second or lower downwardly depending compartment 26, having the upper end thereof in open communication with the upper compartment 16. This is provided by an elongated opening or slot formed in the bottom wall structure 22 as is shown in more specific detail in the enlarged scale cross-section of FIG. 5 of the drawings. The lower compartment 26 is preferably, although not necessarily, integrally formed with the remaining receptacle structure and, in essence, constitutes an elongated narrow downwardly depending compartment substantially rectangular in cross-section. As illustrated in FIG. 5, the lower compartment 26 includes vertically depending, generally parallel spaced sidewalls 28 wherein the sidewalls are stepped to form a compartment narrowing in steps or increments towards the bottom end thereof. Thus, the upper section 30 of the lower compartment has the sidewalls at a spacing of X, then extending into an intermediate section 32 providing a slightly narrower spacing X' between the sidewalls and which, in turn, extends downwardly into the lowermost section 34 providing an even narrower spacing X" between the sidewalls 28 down towards the bottom end wall 36. At the upper end of the uppermost compartment section 30, the sidewalls 28 are each provided with a chamfer having an angle $\theta$ of approximately 45° widening outwardly towards the juncture of the sidewalls with the bottom wall 22 of the upper compartment 16. Similarly, the upper end of the lowermost section 34 of the lower compartment 26, which forms a shoulder with the intermediate section 32, is provided with an outwardly angled taper $\alpha$ of approximately 11°, for purposes as described hereinbelow.

The receptacle 12 may be constructed of a rigid molded plastic material; for example, a tri-monomer thermoplastic essentially constituted of a combination of acrylonitrile, butadiene, and styrene (ABS), although other suitable molded thermoplastic materials may be readily utilized herein. Alternatively, the receptacle 12 may also be constituted of other suitable materials, such as metal, in conformance with the particular intended condition and use of the bag clamping arrangement.

Insertable into the receptacle 12, in order to form the bag clamping arrangement pursuant to the invention, is the novel bag clamping plate unit 14, which can be clearly ascertained in the various figures of the drawings, and particularly in the detail thereof as shown in FIG. 6.

Specifically, the bag clamping plate unit 14 includes a generally rectangular flat plate member 40 which may be of a height somewhat in excess of the height of the receptacle 12, and which has a length slightly less than the length of the lower compartment 26. Fastened to the opposite sides of the plate 40, and extending proximate the lower end thereof, are a pair of protuberances 42, one located respectively on each side of the plate 40. The protuberances 42, which are generally rectangular in cross-section, may also be integrally formed with the plate 40. Fastened to the outwardly facing surfaces of the protuberances 42 are, in turn, upwardly extending and somewhat outwardly diverging thin plates 44 which are essentially flexible in nature. The plates 44, which are of approximately the same length as the plate 40 but less than the height of the lower compartment 26, each mount at their upper ends a cylindrical member 46 possessing a smooth exterior surface, and with the cylindrical members 46 also each being of a length substantially the same length as that of the plate 40. The height of the cylindrical members 46 above the bottom of the plate 40 is slightly greater than the height of the lowermost section 34 of the lower compartment 26, and is of a width, when the plates 44 are compressed axially, slightly less than the width X' of the compartment section 32. All of the components 40, 42, 44, and 46 may be constructed of a suitable plastic material, such as polycarbonate, or a metal as required, and may be fastened by adhesive bonding, riveting or the like. The upper end of the plate 40 is provided centrally thereof with a gripping portion 48 which may include a substantially cylindrical portion for ease in gripping and with an elongate slot 50 below the gripping portion to allow for the through-passage of the hand or fingers of a user.

Figure 2:
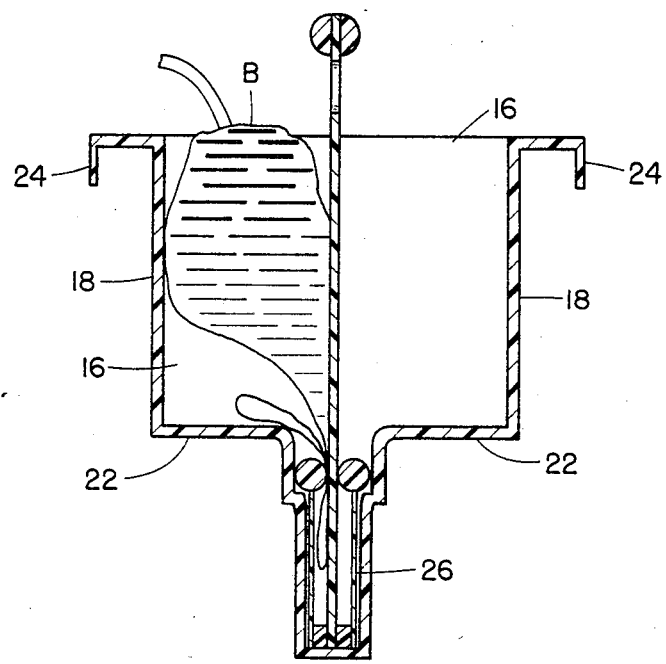
FIG. 2 illustrates a sectional view taken along line 2—2 in FIG. 1 illustrating the bag clamping arrangement utilized for the clamping of a single flexible bag, for example, utilized in a plasma collecting system.
Figure 3:
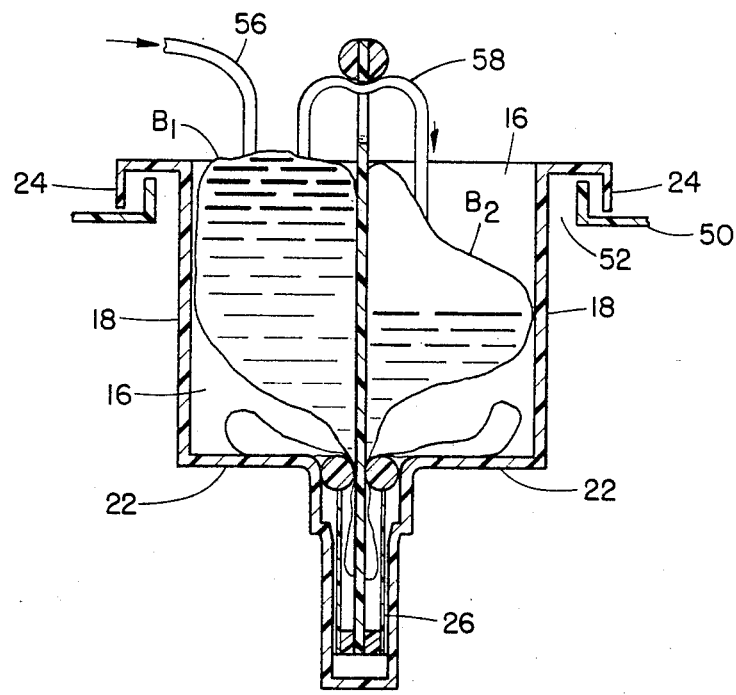
FIG. 3 illustrates a view similar to that of FIG. 2, illustrating the bag clamping arrangement when employed in the clamping of two flexible bags which are interconnected as as to form an overflow system.

The functioning of the bag clamping arrangement 10 is essentially as follows:

The receptacle 12 may be mounted on a suitable support 50 which includes an opening 52 formed by an upstanding encompassing flange adapted to extend into the inverted U-shape formed by the depending flange 24 on the receptacle 12, as shown in FIG. 3, so as to prevent any possible leakage of fluids from the flexible bags into the mounting support 50. The bag clamping arrangement 10 may be used with one or two bags B, in which FIG. 2 shows the use of the arrangement with one flexible bag B, whereas FIGS. 3 and 5 show the arrangement employed with two flexible bags $B_1$ and $B_2$.

As illustrated in FIGS. 3 and 5, the bags $B_1$ and $B_2$ have the bottom ends thereof folded over and inserted between the plate 40 and the respective cylindrical member 46 on either side of the plate 40, such that a portion of the bottom section of the bag will lie on the upper surface of the bottom wall structure 22 of the upper compartment 16 on either side of the clamping plate unit 14. Thereafter, when the clamping unit 14 is moved downwardly in the direction of the arrow as shown in FIG. 5 into the lower compartment 26 such that, when the cylindrical members 46 pass the 45° chamfer $\theta$, they will be biased radially inwardly towards the plate 40 into the gap X in the upper section 30 of the lower compartment 26, the diameters of the cylindrical members 46 and the thickness of plate 40 being dimensioned relative to the width X in the upper section 30 of the compartment 26, to thereby rigidly clamp and seal the bags $B_1$ and $B_2$ between the cylindrical member 46 and the facing surfaces of the plate 40. At this time, filling of the bag $B_1$ may commence through an inlet connection 56 (FIG. 3) which may communicate at its other end with an indwelling catheter or a plasmapheresis device (not shown). Furthermore, a suitable connecting tube 58 is adapted to interconnect the upper ends of bags $B_1$ and $B_2$, which are in the upper compartment 16 one each on both sides of the plate 40, such that when the portion of the bag $B_1$ which is not clamped off by the device 14 is completely filled with fluid, the overflow will then pass through the tube 58 into the second bag $B_2$.

In the event that the bag clamping arrangement 10 is employed with only a single flexible bag B, as illustrated in FIG. 2, the slightly lesser width of the axially compressed plate unit 14, due to the absence of the material thickness of a second bag, will permit the bag B, which is clamped between one cylinder member 46 and the facing surface of plate 40 in the same manner as described with regard to the previous embodiment, to be moved downwardly with the unit 14 into the intermediate section 32 having the slightly narrower width X, the lower compartment 26 so as to cause the cylinders 46 to contact the plate 40 in the intermediate section 32 of the lower compartment.

In order to facilitate the introduction of the lower end of the bag clamping plate unit 14 into the bottom section 34 of the lower compartment 26, the latter is provided with a taper $\alpha$ of approximately 11° between the lowermost section 34 and the intermediate section 32, this taper acting as a guide surface for ensuring easy insertability of the plate unit 14 into the lower compartment.

The bag clamping plate unit 14, including the resilient plates 44, may be constituted of a material similar to that of the receptacle 12, or alternatively, of a suitable metal and/or plastic material such as polycarbonate.

The inventive bag clamping arrangement 10 may be attached to or mounted on an accurate weighing system (not shown) in which the volume of fluid or liquid collected in the bag or bags can be readily calculated from the weight and specific gravity of the contents.

Although the foregoing arrangement has been described particularly in connection with a urine collecting system or a plasmapheresis device, many other uses in hospital and medical practice readily lend themselves to the invention. Thus, such uses may contemplate the employment of the arrangement in closed circuit urine collection, chest drainage, abdominal fluid drainage, and gastric fluid collection, among various other utilitarian applications.

While there have been shown and described what are considered to be preferred embodiments of the invention, it will of course be understood that various modifications and changes in form or detail could readily be made without departing from the spirit of the invention. It is therefore intended that the invention be not limited to the exact form and detail herein shown and described, nor to anything less than the whole of the invention herein disclosed as hereinafter claimed.

What is claimed is:

1. A bag clamping arrangement for automatically clamping and controlling the filling volume in end overflow of fluid from at least one closed flexible bag; comprising, in combination:
(a) a rigid, upwardly open receptacle having an upper compartment of generally parallel piped configuration; and a lower vertically downwardly depending compartment communicating with a bottom opening in said upper compartment, said flexible bag being insertable into said receptacle such that a portion of the bag is located in the upper compartment and a portion of the bag depends into the lower compartment;
(b) and bag clamping means being insertable into said receptacle, said bag clamping means including a vertically oriented plate member downwardly movable through said upper compartment with the lower end portion thereof insertable into said lower compartment; and resilient biasing means fastened to said lower end portion of the plate member, said bag extending between the resilient biasing means and said plate member, whereby the positioning of the lower end portion of said plate member in the lower compartment will bias said resilient biasing means towards the plate member and effect the clamping of the bag therebetween.

2. A bag clamping arrangement as claimed in claim 1, wherein said lower compartment is a narrow compartment in cross-section extending substantially centrally across the width of said receptacle, the width of the lowermost end section of said lower compartment being in substantial conformance with the width of the lower end of said bag clamping means.

3. A bag clamping arrangement as claimed in claim 2, wherein said lower compartment has an intermediate section wider than the lowermost section of said compartment, and an upper section wider than said intermediate section communicating with the opening in the bottom of said upper compartment, said opening being in conformance with the cross-sectional area of said upper section of the lower compartment.

4. A bag clamping arrangement as claimed in claim 3, wherein one flexible bag is inserted into said receptacle, said bag clamping means clamping said bag in the intermediate section of said lower compartment.

5. A bag clamping arrangement as claimed in claim 3, wherein two flexible bags are inserted into said receptacle one each on respectively the opposite sides of said plate member, said bag clamping means clamping said bags in the upper section of said lower compartment.

6. A bag clamping arrangement as claimed in claim 1, wherein said plate member includes protuberances extending sideways along the lower end thereof; said biasing means including upwardly and outwardly diverging flexible plates having their lower ends fastened to said protuberances on both sides of said plate member, and cylinder means being fastened to and extending along the upper edge of each said resilient plates, the lower portion of said flexible bag depending between said cylinder means and flexible plate and the facing surface of said plate member for clamping engagement therebetween at insertion of said bag clamping means into said lower compartment.

7. A bag clamping arrangement as claimed in claim 3, wherein an outwardly sloping chamfer is formed along the upper end of the walls of the upper section of said lower compartment communicating with the opening in the bottom of said upper compartment to facilitate insertion of the biasing means into the lower compartment of said receptacle.

8. A bag clamping arrangement as claimed in claim 7, wherein said chamfer subtends an angle of about 45° with the vertical direction orientation of said lower compartment.

9. A bag clamping arrangement as claimed in claim 3, wherein an outwardly diverging taper is formed at the upper end of the lowermost end section towards the intermediate section of said lower compartment to facilitate insertion of the lower end of said bag clamping means into said lowermost end section.

10. A bag clamping arrangement as claimed in claim 9, wherein said taper subtends an angle of about 11° with the vertical orientation of said lower compartment.

11. A bag clamping arrangement as claimed in claim 1, wherein said receptacle includes an encompassing flange peripherally extending about the upper edge thereof, said flange being of an essentially inverted U-shape in cross-section for supporting said receptacle on a complementary edge of a mounting support.

12. A bag clamping arrangement as claimed in claim 1, wherein handgrip means is formed proximate the upper edge of said plate member to allow for manipulation of said bag clamping means.

13. A bag clamping arrangement as claimed in claim 1, wherein said receptacle and said bag clamping means are constituted of a plastic material.

14. A bag clamping arrangement as claimed in claim 13, wherein said receptacle is formed of a tri-monomer plastic essentially constituted of acrylonitrile, butadiene and styrene.

15. A bag clamping arrangement as claimed in claim 13, wherein said bag clamping means is constituted of polycarbonate.

16. A bag clamping arrangement as claimed in claim 5, wherein one said flexible bag is connected to receive fluid from a fluid supply source, and said second flexible bag is connected to said first flexible bag for receiving fluid overflow therefrom.

17. A bag clamping arrangement as claimed in claim 1, for use with a closed urine collection system, a plasmapheresis device, chest drainage system, abdominal fluid drainage system, or gastric fluid collection system.

* * * * *